United States Patent
Riggio et al.

(10) Patent No.: US 10,874,761 B2
(45) Date of Patent: Dec. 29, 2020

(54) SANITATION METHOD AND SYSTEM (71) Applicant: THOMAS JEFFERSON UNIVERSITY, Philadelphia, PA (US)

(72) Inventors: Jeffrey Riggio, Wynnewood, PA (US); Robert Neff, Villanova, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 251 days.

(21) Appl. No.: 15/771,988

(22) PCT Filed: Oct. 28, 2016

(86) PCT No.: PCT/US2016/059280
§ 371 (c)(1),
(2) Date: Apr. 27, 2018

(87) PCT Pub. No.: WO2017/075326
PCT Pub. Date: May 4, 2017

(65) Prior Publication Data
US 2018/0221527 A1    Aug. 9, 2018

Related U.S. Application Data

(60) Provisional application No. 62/247,426, filed on Oct. 28, 2015.

(51) Int. Cl.
*G05B 1/00* (2006.01)
*G01D 11/26* (2006.01)
(Continued)

(52) U.S. Cl.
CPC .............. *A61L 2/28* (2013.01); *A61L 2/16* (2013.01); *G08B 21/245* (2013.01); *G16H 40/20* (2018.01); *A61L 2202/14* (2013.01)

(58) Field of Classification Search
CPC ....... G08B 21/245; A61L 2/0082; A61L 2/16; A61L 2/18; A61L 2202/10
(Continued)

(56) References Cited

U.S. PATENT DOCUMENTS 6,236,953 B1 * 5/2001 Segal .................. G07C 1/10
702/127
2009/0301167 A1   12/2009 Priestman et al.
(Continued)

OTHER PUBLICATIONS

International Search Report and Written Opinion issued in International Application No. PCT/US2016/059280 dated Feb. 16, 2017.

*Primary Examiner* — Monzer R Chorbaji
(74) *Attorney, Agent, or Firm* — Cozen O'Connor (57) ABSTRACT

A sanitation system may include a sink, a sanitation material dispenser for dispensing material such as soap, and a dryer for either dispensing dryer material such as paper towels or providing heated air. An electronic device may be in communication with one or more of these items, and a sanitation module may operate on the sanitation system. The sanitation module may time a sanitation activity for the sanitation system, such as hand washing. Content may be displayed on the electronic device, and the content may serve to engage or distract the user. The electronic device may be able to identify the individual user and customize the content. The sanitation module may time the sanitation procedure and may accordingly promote a minimum time spent on the sanitation activity. The sanitation system may also be used for monitoring either the sanitation material or the dryer material and automatically order new material when the material is low.

5 Claims, 6 Drawing Sheets

(51) Int. Cl.
  *B08B 7/00*    (2006.01)
  *A61L 2/28*    (2006.01)
  *G16H 40/20*   (2018.01)
  *G08B 21/24*   (2006.01)
  *A61L 2/16*    (2006.01)

(58) Field of Classification Search
  USPC .......... 134/6, 22.1, 56 R, 58 R, 113, 166 R;
                 422/1, 28, 105, 119, 292, 300
  See application file for complete search history.

(56) References Cited

U.S. PATENT DOCUMENTS

| | | |
|---|---|---|
| 2011/0291840 A1 | 12/2011 | Pelland et al. |
| 2011/0316703 A1 | 12/2011 | Butler et al. |
| 2012/0112906 A1 | 5/2012 | Borke et al. |
| 2014/0104062 A1 | 4/2014 | Weiner |
| 2015/0161874 A1 | 6/2015 | Thyroff et al. |
| 2015/0194043 A1 | 7/2015 | Dunn et al. |

\* cited by examiner

SANITATION METHOD AND SYSTEM

CROSS REFERENCE TO RELATED APPLICATIONS

This application claims priority to U.S. Provisional Patent Application No. 62/247,426 filed on Oct. 28, 2015, the entire contents of which are herein incorporated by reference.

FIELD OF THE DISCLOSURE

This disclosure relates generally to methodologies to ensure hand hygiene through implementation of systems and methods to occupy a subject for a predetermined time and facilitate hygienic activity protocols for a duration of time.

BACKGROUND

Proper and effective hand washing procedure typically requires hands to be washed with soap for twenty (20) seconds or longer. While this is a well understood requirement, adherence is often poor. Centers of Disease Control and Prevention estimates health-care-related infections yearly affected nearly 650,000 Americans and led to about 75,000 deaths. Appropriate hand hygiene is proven to help prevent infections and the spread of communicable disease. Unfortunately, studies show that on average, only a small subset of healthcare, food preparation, and other workers requiring high standards of hygiene actually clean their hands as often as they should. In particular, most people do not wash for the recommended twenty (20) seconds, and many wash for less than ten (10) seconds, a time that is insufficient for proper cleaning.

BRIEF SUMMARY OF THE DISCLOSURE

The following presents a simplified summary of the disclosure in order to provide a basic understanding of some aspects of the invention. This summary is not an extensive overview of every embodiment disclosed herein. It is intended to neither identify key or critical elements of the various embodiments nor delineate the scope of the disclosure. Its sole purpose is to present some concepts of the disclosure, in accordance with the various embodiments disclosed herein, in a simplified form as a prelude to the more detailed description that is presented later.

In one embodiment of the disclosure, a sanitation system for conducting a sanitation activity may include a sink, a dispenser for dispensing a sanitation material, a sensor in communication with either the sink or the dispenser with the sensor operable to detect activation of either the sink or the dispenser, and an electronic multifunction device in electronic communication with the sensor. The electronic multifunction device may include an output device, a processor, and memory. The sensor may signal the electronic multifunction device of activation of either the dispenser or the sink thereby initiating a sanitation module operating on the electronic multifunction device.

In another embodiment of the disclosure, a sanitation system may include a sink, a dispenser for dispensing a sanitation material and the dispenser may include a dispenser sensor operable to detect activation of the dispenser and control operation of the dispenser, a dryer for either dispensing dryer material or for blowing hot air and the dryer including a dryer sensor operable to detect activation of the dryer and to control operation of the dryer, and an electronic multifunction device in electronic communication with the dispenser sensor and the dryer sensor, with the electronic multifunction device including a display, a processor, and memory. A sanitation module may operate on the electronic multifunction device and may be in communication with the dispenser sensor and the dryer sensor. The sanitation module may be operable to monitor the length of a sanitation activity beginning with an activation event and ending with an ending event, alert a user of the sanitation system when the user has not conducted the sanitation activity for a predetermined amount of time, and identify the user and store user data regarding the user's use of the sanitation system. The activation event may be either the dispensing of sanitation material or the activation of the sink.

In an additional embodiment of the disclosure, a method of conducting a sanitation procedure may include providing an electronic multifunction device in a sanitation environment, the sanitation environment may include a sink and a dispenser for dispensing a sanitation material, the electronic multifunction device may be operable to monitor the dispenser, and the electronic multifunction device may include a display, a processor, and memory. The method further include activating the dispenser the dispenser thereby defining an activation event, monitoring for an ending event of the sanitation procedure, determining the length of time between the activation event and the ending event, alerting the user of a premature finish to the sanitation procedure if the length of time between the activation event and the ending event is less than a predetermined length of time, and providing media content on the display upon the activation event.

In a further embodiment of the disclosure, a method for maintaining a sanitation environment may include providing an electronic multifunction device, a sink, and a sanitation material dispenser in the sanitation environment, the electronic multifunction device operable to monitor the sink and the sanitation material dispenser, the electronic multifunction device including a display, a processor, and memory. The method may further include monitoring the amount of sanitation material in the sanitation material dispenser, and transmitting an alert from the electronic multifunction device to a remote computer when the sanitation material falls below a predetermined level.

The following description and the annexed drawings set forth certain illustrative aspects of the embodiments of the disclosure. These aspects are indicative, however, of but a few of the various ways in which the principles of the disclosure may be employed and the various embodiments are intended to include all such aspects and their equivalents. Other advantages and novel features will become apparent from the following description when considered in conjunction with the drawings.

DETAILED DESCRIPTION

The following detailed description and the appended drawings describe and illustrate some embodiments of the disclosure for the purpose of enabling one of ordinary skill in the relevant art to make and use these embodiments. As such, the detailed description and illustration of these embodiments are purely illustrative in nature and are in no way intended to limit the scope of the disclosure in any manner. It should also be understood that the drawings are not necessarily to scale and in certain instances details may have been omitted, which are not necessary for an understanding of the embodiments, such as details of fabrication and assembly. In the accompanying drawings, like numerals represent like components.

In one embodiment of the disclosure, a sanitation system for conducting a sanitation activity may include a sink, a dispenser for dispensing a sanitation material, a sensor in communication with either the sink or the dispenser, with the sensor operable to detect activation of either the sink or the dispenser, and an electronic multifunction device in electronic communication with the sensor. The electronic multifunction device may include an output device, a processor, and memory. The sensor may signal the electronic multifunction device of activation of either the dispenser or the sink thereby initiating a sanitation module operating on the electronic multifunction device.

In further embodiments, the output device may be a display, and engagement content may be provided on the display during the sanitation activity. The sanitation module may be operable to monitor the length of time of the sanitation activity, the sanitation activity beginning with the activation of either the dispenser or the sink and ending with an ending event. The system may include a dryer operable to either dispense dryer material or heated air, the dryer including a dryer sensor operable to monitor the activation of the dryer, and the ending event may occur by the activation of the dryer. The sensor may be operable to determine when water no longer flows from the sink, and the ending event may occur by the cessation of water flowing from the sink. The electronic multifunction device may include an input device, wherein the input device and the output device are both a touchscreen display. The electronic multifunction device may include an input device. The sanitation module may identify a user of the sanitation system from user data provided through the input device, and the sanitation module adjusts the functionality of either the dispenser or the sink in response to the identification of the user. The multifunction electronic device may be in further communication with a remote computer, the remote computer having a database of user data. The database of user data may include electronic medical records. The output device may alert a user of the sanitation system if the time between the activation event and the ending event is less than a predetermined amount of time. The sensor may monitor and transmit data regarding either the use of water by the sink or the use of sanitation material dispensed by the dispenser.

In another embodiment of the disclosure, a sanitation system may include a sink, a dispenser for dispensing a sanitation material and the dispenser may include a dispenser sensor operable to detect activation of the dispenser and control operation of the dispenser, a dryer for either dispensing dryer material or for blowing hot air and the dryer including a dryer sensor operable to detect activation of the dryer and to control operation of the dryer, and an electronic multifunction device in electronic communication with the dispenser sensor and the dryer sensor, with the electronic multifunction device including a display, a processor, and memory. A sanitation module may operate on the electronic multifunction device and may be in communication with the dispenser sensor and the dryer sensor. The sanitation module may be operable to monitor the length of a sanitation activity beginning with an activation event and ending with an ending event, alert a user of the sanitation system when the user has not conducted the sanitation activity for a predetermined amount of time, and identify the user and store user data regarding the user's use of the sanitation system. The activation event may be either the dispensing of sanitation material or the activation of the sink.

In further embodiments, the ending event may occur from the activation of the dryer. The electronic multifunction device may be in further communication with a remote computer, and the user data includes electronic medical records. The display may begin outputting media content with the activation event. The media content may be customizable by the individual user through onsite interaction with the user. The sanitation module may be operable to identify the user as a particular person from a user database. The sanitation module may adjust the operation of at least one of the sink, the dispenser, or the dryer in response to the identification of the particular person. The user database may include electronic medical records.

In another embodiment, a method of conducting a sanitation procedure may include providing an electronic multifunction device in a sanitation environment, the sanitation environment may include a sink and a dispenser for dispensing a sanitation material, the electronic multifunction device may be operable to monitor the dispenser, and the electronic multifunction device may include a display, a processor, and memory. The method further include activating the dispenser the dispenser thereby defining an activation event, monitoring for an ending event of the sanitation procedure, determining the length of time between the activation event and the ending event, alerting the user of a premature finish to the sanitation procedure if the length of time between the activation event and the ending event is less than a predetermined length of time, and providing media content on the display upon the activation event.

In further embodiments, the method may include identifying a user of the sanitation procedure from user data access by the electronic multifunction device from a user database, the user database including electronic medical records, and adjusting the sanitation procedure such as the sanitation materials utilized, volume of such materials, or the predetermined length of time based on the user data. The identifying a user may also include customizing media content provided on the display of the electronic multifunction device. A dryer may be provided to either produce heated air or dispense drying material, the electronic multifunction device further operable to monitor activation of the dryer, and the ending event may be defined by activation of the dryer.

Embodiments of applications executed by portable multifunction devices, user interfaces for such devices, and associated processes for using such devices are described. In some embodiments, the device is a portable communications device such as a mobile telephone that also contains other functions, such as PDA and/or music player functions. The device may also be a tablet, smart phone, or the like.

In additional embodiments, a method for maintaining a sanitation environment may include providing an electronic multifunction device, a sink, and a sanitation material dispenser in the sanitation environment, the electronic multifunction device operable to monitor the sink and the sanitation material dispenser, the electronic multifunction device including a display, a processor, and memory. The method may further include monitoring the amount of sanitation material in the sanitation material dispenser, and transmitting an alert from the electronic multifunction device to a remote computer when the sanitation material falls below a predetermined level.

In further embodiments, the transmitting may include transmitting location data in order to identify the location of the sanitation material dispenser. The method may include providing a dryer for dispensing dryer material, the electronic multifunction device further operable to monitor the amount of dryer material remaining in the dryer, monitoring the amount of dryer material remaining in the dryer, and transmitting an alert from the electronic multifunction device to a remote computer when the dryer material falls below a predetermined level. The monitoring of the dryer and the sanitation material dispenser may be conducted in real time For simplicity, in the discussion that follows, an electronic multifunction device may be a prior art portable electronic multifunction device, or may include components found in prior art multifunction devices such as a touch screen. A prior art portable multifunction device such as an iPhone™ or the device disclosed in U.S. Pat. No. 7,479,949 can be used to execute the applications of the present invention. The applications can also be executed in portable multifunction devices that do not include a touch screen for inputting information, but that rely instead on a more conventional mechanism, for example point-and-click, keypad, keyboard, or click-wheel mechanisms.

In addition to supporting the applications of the disclosed embodiments, the portable multifunction device described below can support a variety of applications, such as one or more of the following: a telephone application, a video conferencing application, an e-mail application, an instant messaging application, a blogging application, a photo management application, a digital camera application, a digital video camera application, a web browsing application, a digital music player application, and/or a digital video player application.

Figure 1:
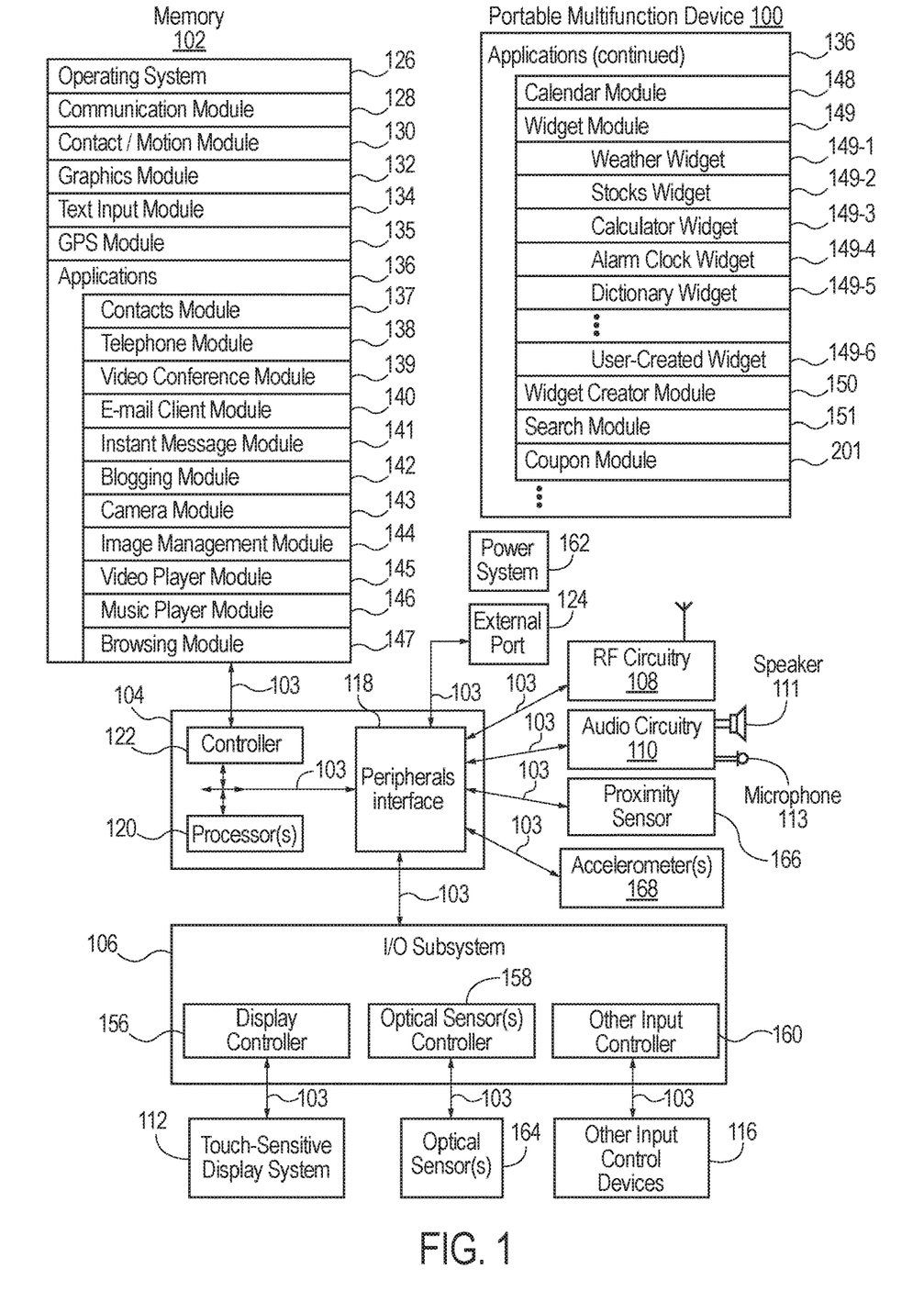
FIG. 1 is a block diagram illustrating a portable multifunction device with a touch-sensitive display in accordance with some embodiments of the disclosure.

FIG. 1 is a block diagram illustrating an exemplary prior art portable multifunction device 100 with a touch-sensitive display 112 modified to include the applications of the present invention. The touch-sensitive display 112 is also known in the art as a touch screen or a touch-sensitive display system. The device 100 may include a memory 102 (which may include one or more computer readable storage mediums, including a tangible non-transitory computer readable medium or media), a memory controller 122, one or more processing units (CPU's) 120, a peripherals interface 118, RF circuitry 108, audio circuitry 110, a speaker 111, a microphone 113, an input/output (I/O) subsystem 106, other input or control devices 116, and an external port 124. The device 100 may include one or more optical sensors 164. These components may communicate over one or more communication buses or signal lines 103.

The device 100 is only one example of a portable multifunction device 100 that may be used to execute the applications of the present invention, and that the device 100 may have more or fewer components than shown, may combine two or more components, or a may have a different configuration or arrangement of the components. The various components shown in FIG. 1 may be implemented in hardware, software or a combination of both hardware and software, including one or more digital signal processing ("DSP") circuits and/or application specific integrated circuits ("ASICs").

Memory 102 may include high-speed random access memory and may also include non-volatile memory, such as one or more magnetic disk storage devices, flash memory devices, or other non-volatile solid-state memory devices. Access to memory 102 by other components of the device 100, such as the CPU 120 and the peripherals interface 118, may be controlled by the memory controller 122.

The peripherals interface 118 couples the input and output peripherals of the device 100 to the CPU 120 and memory 102. The one or more processors 120 run or execute various software programs and/or sets of instructions stored in memory 102 to perform various functions for the device 100 and to process data.

The peripherals interface 118, the CPU 120, and the memory controller 122 may be implemented on a single chip, such as a chip 104. They may also be implemented on separate chips.

The transceiver circuitry 108 receives and sends electromagnetic signals. A person of ordinary skill in the art would recognize that these signals are conventionally referred to as radio frequency ("RF") signals in the context of portable devices, regardless of whether the signals fall within what is conventionally known as the radio spectrum. The term transceiver circuitry and RF circuitry will be used interchangeably in the present application.

The RF circuitry 108 converts electrical signals to/from electromagnetic signals and communicates information to and from communications networks and other communications devices by modulating/demodulating electromagnetic signals with data corresponding to the information. The RF circuitry 108 may include circuitry known in the art for performing these functions, including but not limited to an antenna system, one or more amplifiers, filters, a tuner, one or more oscillators, a digital signal processor, a CODEC chipset, modulator/demodulator, a subscriber identity module (SIM) card, memory, and so forth. The RF circuitry 108 may communicate with networks, such as the Internet, an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this application.

The audio circuitry 110, the speaker 111, and the microphone 113 provide an audio interface between a user and the device 100. The audio circuitry 110 receives audio data from the peripherals interface 118, converts the audio data to an electrical signal, and transmits the electrical signal to the speaker 111. The speaker 111 converts the electrical signal to human-audible sound waves. The audio circuitry 110 also receives electrical signals converted by the microphone 113 from sound waves. The audio circuitry 110 converts the electrical signal to audio data and transmits the audio data to the peripherals interface 118 for processing. Audio data may be retrieved from and/or transmitted to memory 102 and/or the RF circuitry 108 by the peripherals interface 118. The audio circuitry 110 may also include a headset jack. The headset jack provides an interface between the audio circuitry 110 and removable audio input/output peripherals, such as output-only headphones or a headset with both output (e.g., a headphone for one or both ears) and input (e.g., a microphone).

The I/O subsystem 106 couples input/output peripherals on the device 100, such as the touch screen 112 and other input/control devices 116, to the peripherals interface 118. The I/O subsystem 106 may include a display controller 156 and one or more input controllers 160 for other input or control devices. The one or more input controllers 160 receive/send electrical signals from/to other input or control devices 116. The other input/control devices 116 may include physical buttons (e.g., push buttons, rocker buttons, etc.), dials, slider switches, joysticks, click wheels, and so forth. Input controller(s) 160 may also be coupled to any (or none) of the following: a keyboard, infrared port, USB port, and a pointer device such as a mouse.

The touch-sensitive touch screen 112 provides an input interface and an output interface between the device and a user. The display controller 156 receives and/or sends electrical signals from/to the touch screen 112. The touch screen 112 displays visual output to the user. The visual output may include graphics, text, icons, video, and any combination thereof (collectively termed "graphics").

A touch screen 112 has a touch-sensitive surface, sensor or set of sensors that accepts input from the user through tactile contact. The touch screen 112 and the display controller 156 (along with any associated modules and/or sets of instructions in memory 102) detect contact (and any movement or breaking of the contact) on the touch screen 112 and converts the detected contact into interaction with user-interface objects (e.g., one or more soft keys, icons, web pages or images) that are displayed on the touch screen. For example, a point of contact between a touch screen 112 and the user corresponds to a finger of the user.

The touch screen 112 may use LCD (liquid crystal display) technology, or LPD (light emitting polymer display) technology, although other display technologies may also be used. The touch screen 112 and the display controller 156 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 112.

The device 100 also includes a power system 162 for powering the various components. The power system 162 may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

The device 100 may also include one or more optical sensors 164. FIG. 1 shows an optical sensor coupled to an optical sensor controller 158 in I/O subsystem 106. The optical sensor 164 may include charge-coupled device (CCD) or complementary metal-oxide semiconductor (CMOS) phototransistors. The optical sensor 164 receives light from the environment, projected through one or more lens, and converts the light to data representing an image. In conjunction with an imaging module 143 (also called a camera module), the optical sensor 164 may capture still images or video. The optical sensor may be located on the back of the device 100, opposite the touch screen display 112 on the front of the device, so that the touch screen display may be used as a viewfinder for either still and/or video image acquisition. An optical sensor may also be located on the front of the device so that the user's image may be obtained for videoconferencing while the user views the other video conference participants on the touch screen display. Preferably, the position of the optical sensor 164 can be changed by the user (e.g., by rotating the lens and the sensor in the device housing) so that a single optical sensor 164 may be used along with the touch screen display for both video conferencing and still and/or video image acquisition.

The device 100 may also include one or more proximity sensors 166. FIG. 1 shows a proximity sensor 166 coupled to the peripherals interface 118. Alternately, the proximity sensor 166 may be coupled to an input controller 160 in the I/O subsystem 106. The proximity sensor 166 may be used to turn off and disable the touch screen 112 when the multifunction device is placed near the user's ear (e.g., when the user is making a phone call). The proximity sensor can also be used to keep the screen off when the device is in the user's pocket, purse, or other dark area to prevent unnecessary battery drainage when the device is a locked state.

The device 100 may also include one or more accelerometers 168. FIG. 1 shows an accelerometer 168 coupled to the peripherals interface 118. Alternately, the accelerometer 168 may be coupled to an input controller 160 in the I/O subsystem 106. The accelerometer 168 captures data that is analyzed to determine whether to change a view of information, for example from portrait to landscape, displayed on the screen of the portable device.

The software components stored in memory 102 may include an operating system 126, a communication module (or set of instructions) 128, a contact/motion module (or set of instructions) 130, a graphics module (or set of instructions) 132, a text input module (or set of instructions) 134, a Global Positioning System (GPS) module (or set of instructions) 135, and applications (or set of instructions) 136.

The operating system 126 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

The communication module 128 facilitates communication with other devices over one or more external ports 124 and also includes various software components for handling data received by the RF circuitry 108 and/or the external port 124. The external port 124 (e.g., Universal Serial Bus (USB), FIREWIRE, etc.) is adapted for coupling directly to other devices or indirectly over a network (e.g., the Internet, wireless LAN, etc.).

The contact/motion module 130 may detect contact with the touch screen 112 (in conjunction with the display controller 156) and other touch sensitive devices (e.g., a touchpad or physical click wheel). The contact/motion module 130 includes various software components for performing various operations related to detection of contact, such as determining if contact has occurred, determining if there is movement of the contact and tracking the movement across the touch screen 112, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/multiple finger contacts). Alternatively the contact/motion module 130 and the controller 160 detect contact on a click wheel, for example.

The graphics module 132 includes various known software components for rendering and displaying graphics on the touch screen 112, including components for changing the intensity of graphics that are displayed. As used herein, the term "graphics" includes any object that can be displayed to a user, including without limitation text, web pages, icons (such as user-interface objects including soft keys), digital images, videos, animations and the like.

The text input module 134, which may be a component of graphics module 132, provides soft keyboards for entering text in various applications (e.g., contacts 137, e-mail 140, IM 141, blogging 142, browser 147, and any other application that needs text input).

The GPS module 135 determines the location of the device and provides this information for use in various applications (e.g., to telephone 138 for use in location-based dialing, to camera 143 and/or blogger 142 as picture/video metadata, and to applications that provide location-based services such as weather widgets, local yellow page widgets, and map/navigation widgets).

The applications modules 136 may include the following modules (or sets of instructions), or a subset or superset thereof: a contacts module 137 (sometimes called an address book or contact list); a telephone module 138; a video conferencing module 139; an e-mail client module 140; an instant messaging (IM) module 141; a blogging module 142; a camera module 143 for still and/or video images; an image management module 144; a video player module 145; a music player module 146; a browser module 147; a calendar module 148; widget modules 149, which may include weather widget 149-1, stocks widget 149-2, calculator widget 149-3, alarm clock widget 149-4, dictionary widget 149-5, and other widgets obtained by the user, as well as user-created widgets 149-6; widget creator module 150 for making user-created widgets 149-6; search module 151; video and music player module, which merges video player module 145 and music player module 146; notes module; and/or map module; and/or online video module.

Examples of other applications 136 that may be stored in memory 102 include other word processing applications, JAVA-enabled applications, encryption, digital rights management, voice recognition, and voice replication.

In conjunction with touch screen 112, display controller 156, contact module 130, graphics module 132, and text input module 134, the contacts module 137 may be used to manage an address book or contact list, including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference 139, e-mail 140, or IM 141; and so forth.

In conjunction with RF circuitry 108, audio circuitry 110, speaker 111, microphone 113, touch screen 112, display controller 156, contact module 130, graphics module 132, and text input module 134, the telephone module 138 may be used to enter a sequence of characters corresponding to a telephone number, access one or more telephone numbers in the address book 137, modify a telephone number that has been entered, dial a respective telephone number, conduct a conversation and disconnect or hang up when the conversation is completed. As noted above, the wireless communication may use any of a plurality of communications standards, protocols and technologies to communicate or transmit data necessary for enacting the features of the embodiments.

In conjunction with RF circuitry 108, audio circuitry 110, speaker 111, microphone 113, touch screen 112, display controller 156, optical sensor 164, optical sensor controller 158, contact module 130, graphics module 132, text input module 134, contact list 137, and telephone module 138, the videoconferencing module 139 may be used to initiate, conduct, and terminate a video conference between a user and one or more other participants.

In conjunction with RF circuitry 108, touch screen 112, display controller 156, contact module 130, graphics module 132, and text input module 134, the e-mail client module 140 may be used to create, send, receive, and manage e-mail. In conjunction with image management module 144, the e-mail module 140 makes it easy to create and send e-mails with still or video images taken with camera module 143.

In conjunction with RF circuitry 108, touch screen 112, display controller 156, contact module 130, graphics module 132, and text input module 134, the instant messaging module 141 may be used to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages and to view received instant messages.

In conjunction with RF circuitry 108, touch screen 112, display controller 156, contact module 130, graphics module 132, text input module 134, image management module 144, and browsing module 147, the blogging module 142 may be used to send text, still images, video, and/or other graphics to a blog (e.g., the user's blog).

In conjunction with touch screen 112, display controller 156, optical sensor(s) 164, optical sensor controller 158, contact module 130, graphics module 132, and image management module 144, the camera module 143 may be used to capture still images or video (including a video stream)

and store them into memory 102, modify characteristics of a still image or video, or delete a still image or video from memory 102.

In conjunction with touch screen 112, display controller 156, contact module 130, graphics module 132, text input module 134, and camera module 143, the image management module 144 may be used to arrange, modify or otherwise manipulate, label, delete, present (e.g., in a digital slide show or album), and store still and/or video images.

In conjunction with touch screen 112, display controller 156, contact module 130, graphics module 132, audio circuitry 110, and speaker 111, the video player module 145 may be used to display, present or otherwise play back videos (e.g., on the touch screen or on an external, connected display via external port 124).

In conjunction with touch screen 112, display system controller 156, contact module 130, graphics module 132, audio circuitry 110, speaker 111, RF circuitry 108, and browser module 147, the music player module 146 allows the user to download and play back recorded music and other sound files stored in one or more file formats, such as MP3 or AAC files.

In conjunction with RF circuitry 108, touch screen 112, display system controller 156, contact module 130, graphics module 132, and text input module 134, the browser module 147 may be used to browse the Internet, including searching, linking to, receiving, and displaying web pages or portions thereof, as well as attachments and other files linked to web pages.

In conjunction with RF circuitry 108, touch screen 112, display system controller 156, contact module 130, graphics module 132, text input module 134, e-mail module 140, and browser module 147, the calendar module 148 may be used to create, display, modify, and store calendars and data associated with calendars (e.g., calendar entries, to do lists, etc.). Suh data and information may be added to a calendar module 148 through importation of data received through the device as generated by individual or total sanitation procedures through the system. This provides mechanism to calendar and connect or automate fulfillment or services such as refilling the modules, cleaning the premises, servicing the components and the like, as non-limiting examples.

In conjunction with RF circuitry 108, touch screen 112, display system controller 156, contact module 130, graphics module 132, text input module 134, and browser module 147, the widget modules 149 are mini-applications that may be downloaded and used by a user (e.g., weather widget 149-1, stocks widget 149-2, calculator widget 149-3, alarm clock widget 149-4, and dictionary widget 149-5) or created by the user (e.g., user-created widget 149-6). A widget may include an HTML (Hypertext Markup Language) file, a CSS (Cascading Style Sheets) file, and a JavaScript file. A widget may also include an XML (Extensible Markup Language) file and a JavaScript file (e.g., Yahoo! Widgets).

In conjunction with RF circuitry 108, touch screen 112, display system controller 156, contact module 130, graphics module 132, text input module 134, and browser module 147, the widget creator module 150 may be used by a user to create widgets (e.g., turning a user-specified portion of a web page into a widget).

In conjunction with touch screen 112, display system controller 156, contact module 130, graphics module 132, and text input module 134, the search module 151 may be used to search for text, music, sound, image, video, and/or other files in memory 102 that match one or more search criteria (e.g., one or more user-specified search terms).

In conjunction with touch screen 112, display controller 156, contact module 130, graphics module 132, and text input module 134, the notes module may be used to create and manage notes, to do lists, and the like.

In conjunction with RF circuitry 108, touch screen 112, display system controller 156, contact module 130, graphics module 132, text input module 134, GPS module 135, and browser module 147, the map module may be used to receive, display, modify, and store maps and data associated with maps (e.g., driving directions; data on stores and other points of interest at or near a particular location; and other location-based data). For example, the precise location of the device and corresponding components can be mapped for fulfillment of orders and/or routine cleaning and maintenance of the premises and/or components of the device.

In conjunction with touch screen 112, display system controller 156, contact module 130, graphics module 132, audio circuitry 110, speaker 111, RF circuitry 108, text input module 134, e-mail client module 140, and browser module 147, the online video module allows the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In other modes of operation, instant messaging module 141, rather than e-mail client module 140, is used to send a link to a particular online video.

In conjunction with various components of device 100 as contemplated with the various embodiments of the disclosure, a sanitation module 201 may be provided in order to communicate with, interrogate, and control a sanitation system.

In one embodiment, each of the above identified modules and applications correspond to a set of instructions for performing one or more functions described above. These modules (e.g., sets of instructions) need not be implemented as separate software programs, procedures or modules, and thus various subsets of these modules may be combined or otherwise re-arranged in various embodiments. For example, video player module 145 may be combined with music player module 146 into a single module (e.g., video and music player module). Memory 102 may store a subset of the modules and data structures identified above. Furthermore, memory 102 may store additional modules and data structures not described above.

The device 100 may be a device where operation of a predefined set of functions on the device is performed exclusively through a touch screen 112 and/or a touchpad. By using a touch screen and/or a touchpad as the primary input/control device for operation of the device 100, the number of physical input/control devices (such as push buttons, dials, and the like) on the device 100 may be reduced.

In other embodiments, a computer may be used to run the various applications and the metrics calculations of the present disclosure. The various embodiments and/or components, for example, the modules, elements, or components and controllers therein, may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field-programmable gate arrays (FPGAs), graphical processing units (GPUs), logic circuits, and any other circuit or processor capable of executing the functions described herein. The above examples are exemplary only, and are thus not intended to limit in any way the definition and/or meaning of the term "computer."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software", "firmware" and "algorithm" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 2:
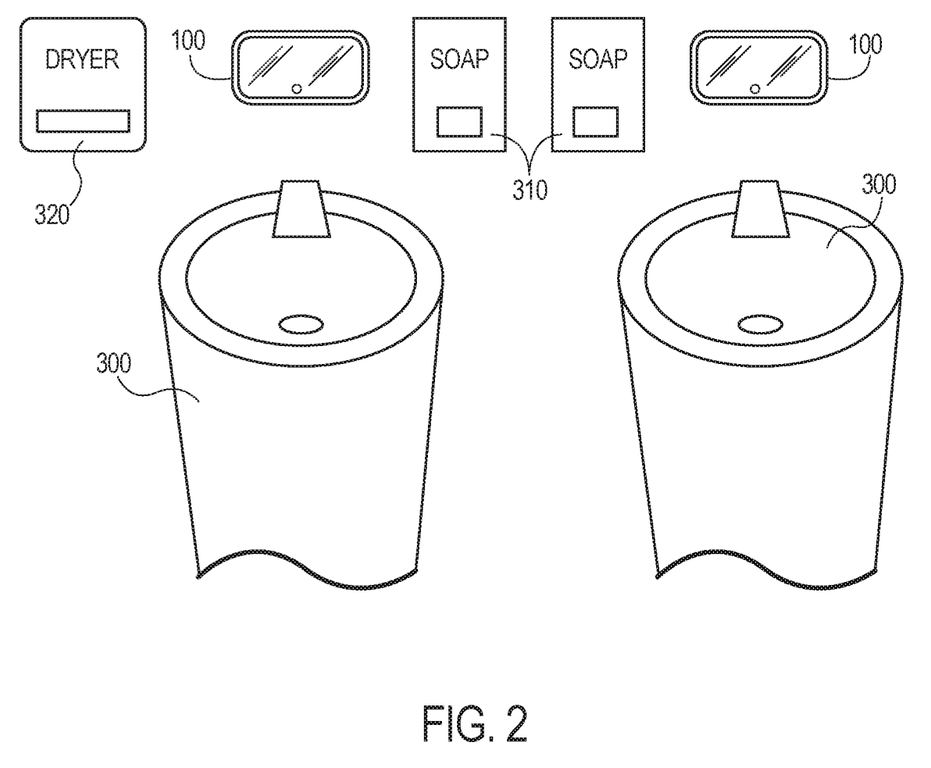
FIG. 2 is a schematic of an embodiment of a sanitation system.
Figure 3:
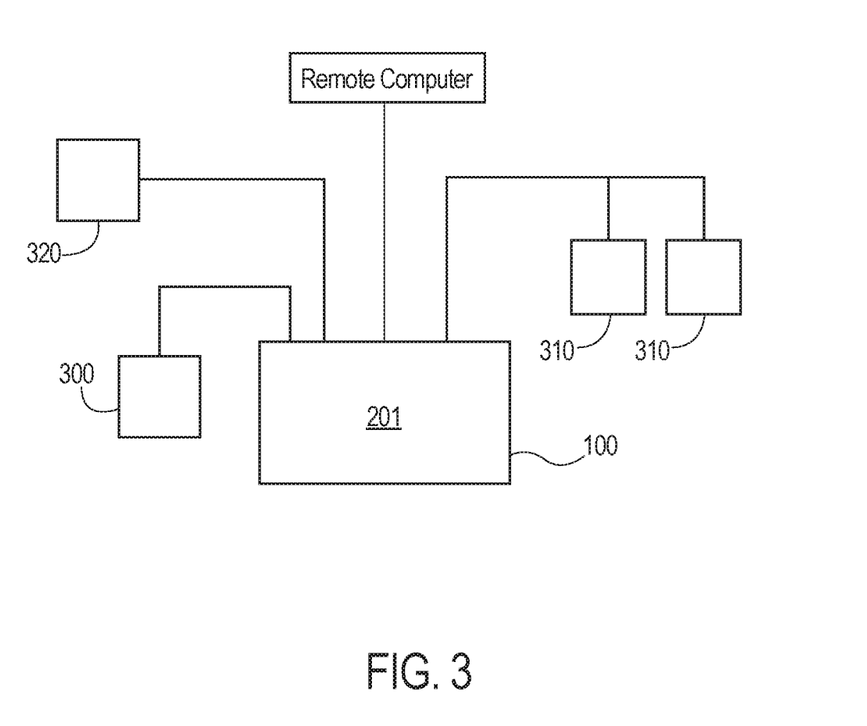
FIG. 3 is a block diagram illustrating electrical communication of the sanitation system of FIG. 2.

With reference to FIGS. 2 and 3, a sanitation system is shown and described in accordance with various embodiments contemplated within the disclosure. An electronic multifunction device 100 may be provided proximate to a sanitation system, which may include one or more sinks 300. As used herein, the term "sink" generally refers to the collective components of a sink, including for instance a drain, basin, faucet, valves, etc. The sanitation system may also include a plurality of dispensers, such as a sanitation material or soap dispenser 310 and a dryer or towel dispenser 320. Other sanitation dispensers are contemplated within the disclosure, such as a mouthwash dispenser, hand sanitizer dispenser, as well as different types of soap dispensers 310 as many be necessary for different classes of individuals using the same sanitation system. For instance, a first soap dispenser 310 could dispense a liquid or other product suitable for a patient and her caregiver while a second dispenser 310 could dispense clinical related content meant for the physician and not the patient. A plurality of each type of dispenser 310, 320 is contemplated within the disclosure, even where only one sink 300 may be provided. Dispensers 310, 320 may also be incorporated into a single housing or a single device, and thus the term "dispenser" as used herein may refer to a multi-function dispenser capable of dispensing towels, sanitation material, heated air, or any other combination or dispenser related items as contemplated within this disclosure.

Various environments are contemplated for sanitation system, including but not limited to restrooms, hospitals, laboratories, and kitchens. In the illustrated embodiment, multifunction device 100 may be a portable multifunction device, such as a tablet, affixed to a wall or surface proximate to each sink 300. Device 100 may also be a computer with one or more components of a portable multifunction device. In other embodiments, the display system 112 may be positioned proximate to a wall or surface, with all or many of the remaining components of device 100 hidden or otherwise remotely connected to display 112, for instance by providing components of device 100 behind or within the wall.

Device 100 may be in electronic communication with electrical components of sink 300, soap dispenser 310, and dryer 320, which all may include sensors of their own in order to facilitate contact free sanitation procedures. The term "sensor" as used herein may generally refer to any condition detecting, monitoring, or controlling device capable of monitoring or controlling one of sink 300, material dispenser 310, and dryer 320. In one embodiment, a sensor may be a motion sensor which operates to active one or more of sink 300, material dispenser 310, or dryer 320. A sensor may also operate to monitor activity such as water flow with sink 300, the amount of material dispensed from or remaining within material dispenser 310, the length of time which dryer 320 is operating, the amount of paper towels in towel dispenser 320. Sink 300 may be an automatic water faucet with communication to device 100. Activation of sink 300, for instance may occur by triggering a motion sensor associated with sink 300, which may initiate sanitation module 201 as described herein. Soap dispenser 310 may be an automatic soap dispenser in communication with device 100. Dryer 320 may be a hand dryer operable to produce a stream of heated air, or dryer 320 may be an automatic paper towel dispenser. Dryer 320 may also be in communication with device 100.

Sanitation module 201 of device 100 may be operable to control or interrogate the components of the sanitation system. Activation of any sanitation component, and in certain embodiments activation of sink 300 or soap dispenser 310, may initiate sanitation module 201. Sanitation module 201 may also be initiated by user interaction with device 100. For instance, device 100 may prompt the user to input identification data prior to beginning the sanitation process. This input may be as simple as the user selecting a type of class the user belongs in. Two non-limiting examples of user classes could be patient and physician or adult and child. The selection could occur through the user's audible signal as dedicated by microphone 113, or the selection could occur by the user selecting an appropriate class icon shown on touch-screen display 112.

In some embodiments, the user could provide individual identifying information so that the particular user can be identified from a database of users, stored either locally in memory 102 or remotely on a remote server or computer. User identification could occur through manual input via touch screen display 112 of identifying information, such as name and date of birth. User identification could also occur through voice or facial recognition software operating on device 100 respectively in conjunction with microphone 113 or camera module 143. User identification could also result from the user presenting a User ID card or other identification object, such as an object to be worn like a lanyard or bracelet or possibly the user's own mobile device, and the object may be scannable for instance utilizing a bar code or QR code to be scanned in conjunction with camera module 143. RFID may also be utilized to identify a particular user by having device 100 read an RFID tag associated with the user. User identification data may include patient records, electronic medical records (EMR), or Electronic Health Record (EHR). Accordingly, device 100 may be linked to a remote computer or server storing EMR or other user data. The sanitation module 201 be specifically adjusted to the individual user upon identification of the user. For instance, sanitation module 201 may require specific sanitation procedures based on a user's condition. Such an embodiment may be particularly utilized in medical facilities such as hospitals, hospices, and nursing care. Examples of a sanitation procedure being modified could be to require a user to conduct a longer sanitation method, to use a first rather than a second type of sanitation material available in sanitation dispenser 310, or may be customizable to adjust the content provided on display 112 as further described herein.

As part of sanitation module 201, a timer may be displayed on display 112. The timer may have a lifespan as determined appropriate by standard recommendations for sanitation activity. For instance, the timer may be twenty (20) seconds in accordance with a recommended time for a person to spend washing her hands. A continuous feedback loop may be established between device 100 and sink 300, and more particularly with the motion sensor of sink 300, so as to detect when a user removes her hands from sink 300 thereby deactivating sink 300. Should the user remove her hands prematurely prior to the completion of the timer, sanitation module 201 may trigger an alert resulting in an audible warning through speaker 111 or a visual warning through display 112 that the user's sanitation activity lasted for an insufficient time. Sanitation module 201 may then prompt the user to resume and finish the sanitation process or completely restart the sanitation process.

Appropriate sanitation procedures can modify several variables including the time of activation of the sink, the type or quantity of sanitation material (soaps or other cleaners), the time for drying or amount of drying materials, and the time between any one or more of the activation of the sensors. For example, while a standard protocol may require a time of 20 seconds or more between a first activation of a sink or dispenser and a dryer, certain protocols may require additional time to confirm that the protocol was completed. For example, a time of 20 seconds may also require that the sink was activated for at least 10 seconds of that time. Protocols can be modified by User ID information, including through RF ID tags or other electronic communication means, or through an appropriate EMR. Modification of any feature of a sanitation procedure can be user based.

In public spaces, a protocol of at least 15 seconds can confirm a completed sanitation protocol, with at least 20 seconds preferred.

As previously described, sanitation module 201 may be activated in some embodiments with user identification, activation of sink 300, or activation of material dispenser 310. Sanitation module 201 may be completed when water is detected as no longer flowing from sink 300, or when a dryer 320 is activated. Sanitation module 201 may provide a first timestamp once a sanitation method has begun, and a second timestamp once a sanitation method has ended. The timestamps may then be measured to arrive at a length of time for the sanitation method.

Device 100 may also be in communication with dispenser 310 and dryer 320. Sanitation module may passively monitor the activation of dispenser 310 and dryer 320 through sensors described herein to ensure they are utilized as part of the sanitation process. Sanitation module 201 may also provide audio or visual prompts to the user at appropriate times in the sanitation process. For instance, if after a predetermined time the user has not yet activated the motion sensor for soap dispenser 310, an audio or visual prompt from device 100 may remind the user to use soap as part of the sanitation process.

In controlling or operating sink 300, dispenser 310, and dryer 320, sanitation module 201 may be able to effectively control the use of these sanitation components thereby reducing wasted resources or ensuring a prompt refilling of materials. For instance, module 201 may automatically turn off sink 300 once the timer has completed, or once dryer 320 is detected as activated, thereby reducing wasted water. Sanitation module 201 may also prevent dryer 320 from operating longer than an approved time or from dispensing an excess number of paper towels. Sanitation module 201 can also control dispenser 310 to ensure no accidental dispensing of material occurs, or to ensure only an approved amount of material is dispensed as part of the sanitation process.

Sanitation module 201 may also monitor these components and collect data to be stored locally in memory 102 or transmitted to a remote computer or server. The monitoring may be in real time, and data transmitted to a remote, operator monitored computer or server may include location data identifying the whereabouts of the sanitation system within a facility. Detection of low material, defined as material remaining in dispenser 310, 320 falling below a predetermined amount, may trigger an alert or warning to be transmitted to a remote computer. An operator at remote computer may in turn order additional material and direct that the material be sent to the low dispenser 310, 320. Alternatively, the process may be automated such that sanitation module 201 may alert a remote computer of a low dispenser 310, 320, and remote computer may transmit order instructions to a vendor, and the order instructions may include location data of the sanitation system. Accordingly, device 100 and sanitation module 201 may effectively monitor sanitation resources, such as water, soap, towels and electricity. This data may be effectively utilized to modify or adjust the sanitation system including sanitation module 201, such as adjusting the timer setting, as well as the sanitation components 300, 310, 320 of the sanitation system thereby increasing effectiveness of the system. Monitoring by sanitation module 201 may also result in detecting low supply of sanitation material, paper towels, etc. Upon a detection of low material, sanitation module 201 may prompt or notify management of the sanitation environment to provide additional material. This notification may be through the display 112 with an alert, such as an icon appearing on display 112, or may be communicated either to the remotely connected computer, to a local LAN or wireless network, or directly to management's personal devices through Bluetooth® for instance.

As part of the sanitation process, device 100 may be able to provide video and/or audio content to distract or entertain the user. For instance, a video or audio clip may be played through display 112 or speakers 111 during the sanitation process. This can be done in conjunction with a displayed countdown timer. This may result in incentivizing the user to complete the sanitation process as well as to more readily engage in the sanitation process. This may also result in occupying or distracting the user during the sanitation process. This media content could be engagement or distraction content such as various jokes, games, images, audio files, video files, websites, news articles, and so forth. This engagement or distraction content could also be educational, such as describing the benefits of washing your hands. This engagement or distraction content could also be individually tailored to the user in embodiments where the user is identified as part of sanitation module 201. For instance, a social media account associated with the user can be displayed. In another example, a physician could review the patient's medical records of the room she is in while she washes her hands. The engagement or distraction content may also be individually tailored to the user through onsite interaction with the user, for instance by prompting the user for a type of joke she prefers to hear, a type of game she prefers to play, relevant educational material, or the type of news she would prefer to be presented with. This content can be tailored to the individual and continually modify based upon data received into the module.

Rewards are also contemplated, such as providing monetary rewards or redeemable points upon successful completion of a sanitation activity. Non-monetary rewards, such as incentives for employees in the form of preferred parking or additional vacation time, is also contemplated. Such rewards can be affiliated with a user file kept in association with the individual users utilizing the sanitation system.

Applying the described embodiments to an example environment of a restroom or other sanitation area, the sanitation system may be able to monitor and track an individual user to ensure they are satisfying environmentally appropriate sanitation procedures, such as a minimum time to wash her hands and ensuring soap was used. The sanitation system may track the user's use of the sanitation system, including monitoring improvements by the user in conducting hand washing protocols. Data collected can be compared to other data collected regarding the sanitation environment in an effort to determine the efficacy of the sanitation system in reducing the spread of infection and communicable illness. Accordingly, reports of user data may be generated as part of sanitation module 201, which for instance may be removed by an environment operator such as a building manager or an employer to objectively determine the efficacy of the sanitation system as well as to track user's use of the system over a specified time period. Data transmission may occur through known or to be developed encryption methods to ensure user data, potentially including highly sensitive EMR, are not intercepted or breached.

The ability of the module to notify a person or alarm when a sanitation procedure was not completed is necessary to ensure sanitary protocols are met in certain industries. For example, in a washroom/toilet, it may be necessary to include a sensor corresponding to the door or to the toilet, wherein activation of either sensor triggers the module to require a complete sanitation protocol to prevent an alarm or alert to a third party or to the system in general. In healthcare and food industries, such a feature can be utilized to enforce proper compliance according to required standards in such industries. A further feature may prevent egress from the washroom/toilet until the sanitation protocol is met.

Figure 4:
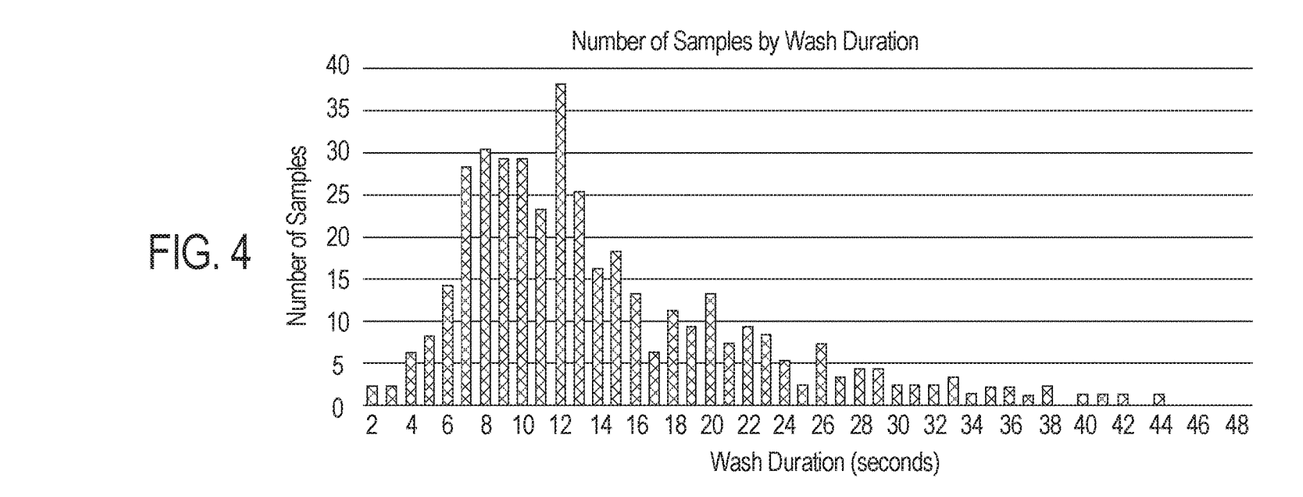
FIG. 4 depicts data of baseline hand washing duration identifying 390 samples, with a mean wash duration of 14 seconds and median wash duration of 12 seconds.
Figure 5:
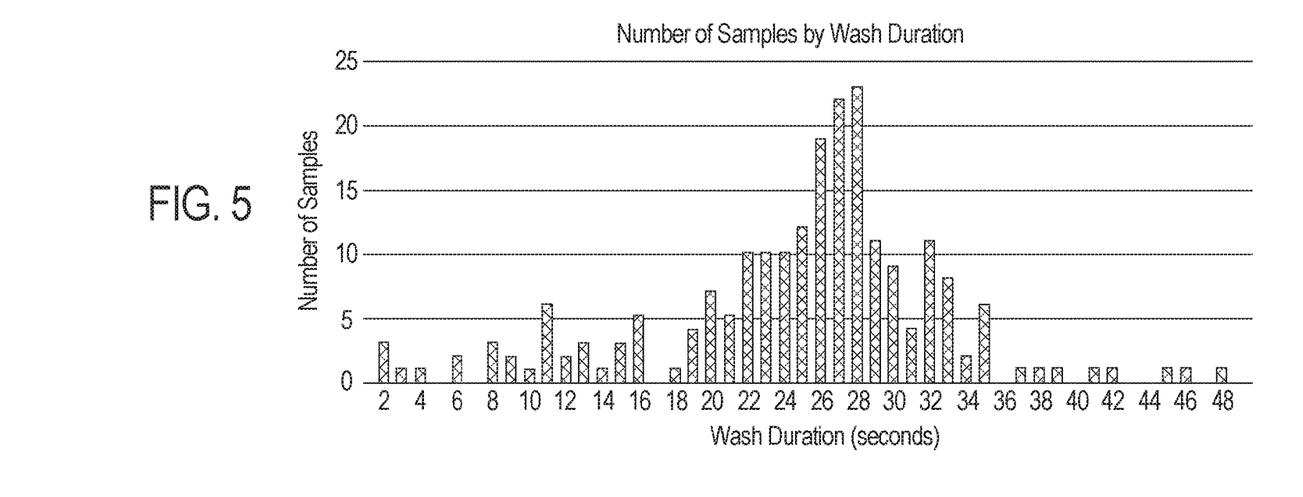
FIG. 5 depicts data after implementation of an embodiment of the present system identifying 213 samples, with a mean wash duration of 25 seconds and median wash duration of 24 seconds.

FIGS. 4-7 detail a study performed using the system described herein. FIG. 4 depicts wherein prior to implementation of the sanitation system in an environment for hand washing, a study was conducted based on 390 samples for hand washing time. Excluding outlier samples above 50 seconds or below 2 seconds, the study found the mean wash duration time to be 14 seconds and the median wash duration to be 12 seconds. This is significantly less than the recommended 20 seconds of wash time for a typical person. Moreover, only 18% of the samples were greater than or equal 20 seconds of hand washing time. This baseline study was conducted over the course of fourteen (14) days and defined a hand washing event as the time from the first soap dispense through the first paper towel tear. This data was collected with a blind sample group. As shown in next in FIG. 5, after incorporating an embodiment of sanitation system disclosed herein, another study was conducted over the course 8 days and 213 samples. The sanitation system sample was taken with a blind sample group. After excluding outlier samples above 50 seconds and below 2 seconds, this sanitation system sample group found the mean wash time to be 25 seconds and the mean wash duration to be 24 seconds. Eighty percent of the samples were greater than or equal to 20 seconds of hand washing time.

Figure 6:
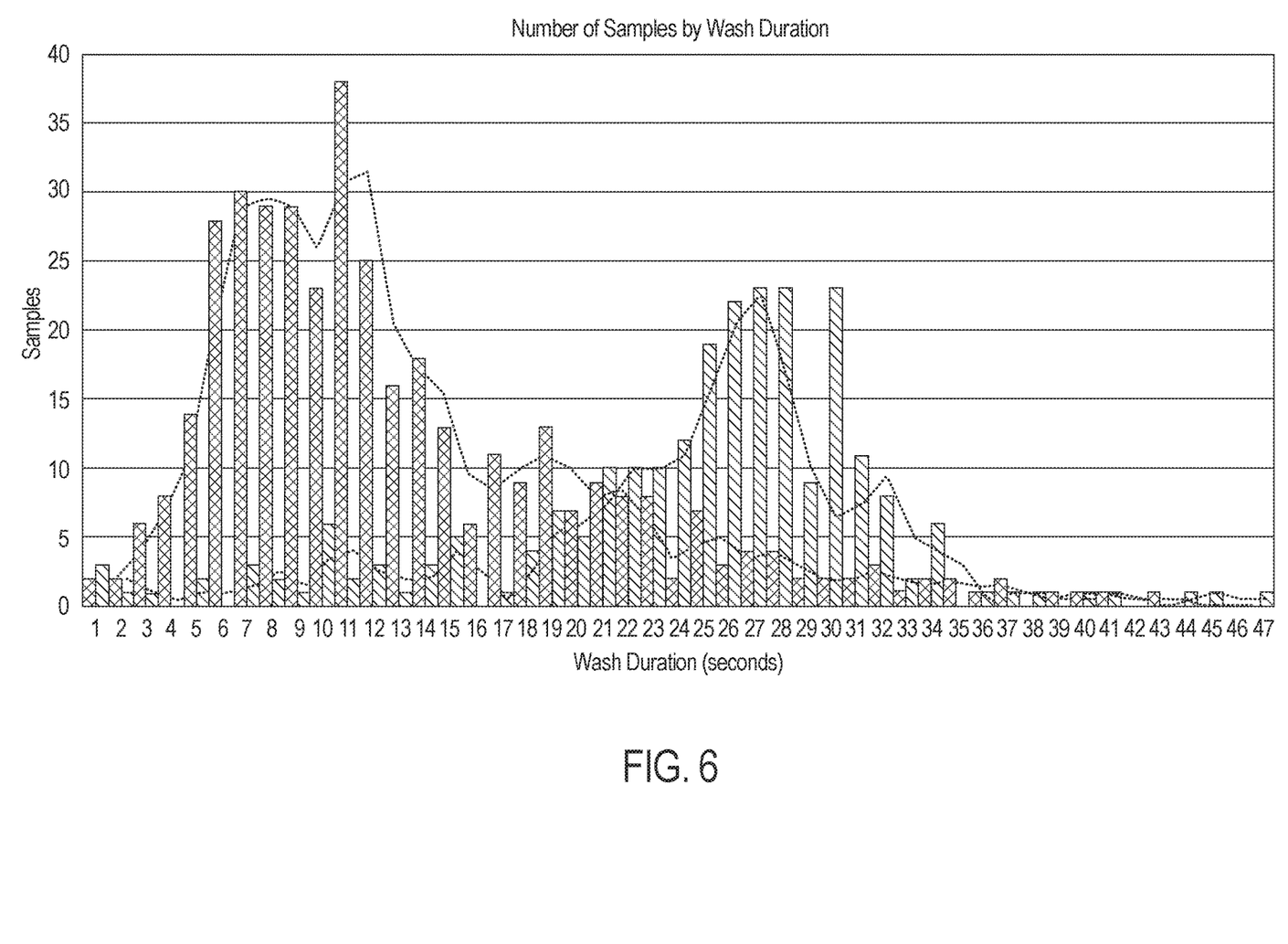
FIG. 6 provides a data overlay of FIGS. 4 and 5.
Figure 7:
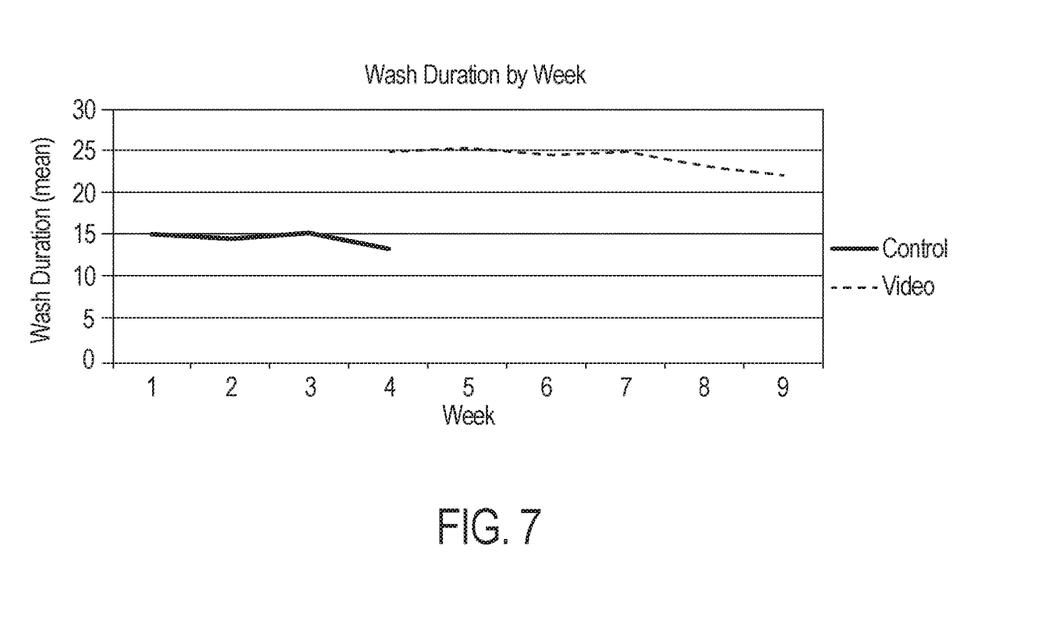
FIG. 7 gives a graphical chart of the mean washing duration pre and post implementation of an embodiment of the system.

FIGS. 6-7 illustrate comparative analysis between the control group and the sanitation system group. FIG. 6 shows a comparison of the data between the baseline group and the sanitation system group showed an increase of 11 seconds mean hand washing time and 12 seconds median hand washing time. Moreover, the sanitation system embodiment resulted in a 344% increase of samples equal to or greater than 20 seconds of hand washing time. FIG. 7 shows a week-to-week comparison of the control group and the sanitation system group, demonstrating not only marked improvement a result of the implementation of the sanitation system, but a lasting effect on the duration of handwashing. With the sanitation system implemented, average hand washing time did not fall below 20 seconds after 4 weeks of the system being implemented.

The descriptions set forth above are meant to be illustrative and not limiting. Various modifications of the embodiments, in addition to those described herein, will be apparent to those skilled in the art from the foregoing description. Such modifications are also intended to fall within the scope of the concepts described herein. Each patent, patent application and publication cited or described in this document are hereby incorporated herein by reference, in their entireties.

The foregoing description of possible implementations consistent with the present disclosure does not represent a comprehensive list of all such implementations or all variations of the implementations described. The description of some implementation should not be construed as an intent to exclude other implementations. For example, artisans will understand how to implement the embodiments in many other ways, using equivalents and alternatives that do not depart from the scope of the disclosure. Moreover, unless indicated to the contrary in the preceding description, none of the components described in the implementations are essential to the embodiments disclosed. It is thus intended that the embodiments be considered as illustrative, with a true scope and spirit of the disclosure being indicated by the following claims.

What is claimed:
1. A method for maintaining a sanitation environment, the method comprising:
providing an electronic multifunction device, a sink, and a sanitation material dispenser in the sanitation environment, the electronic multifunction device operable to monitor the sink and the sanitation material dis- penser, the electronic multifunction device including a display, a processor, and memory;

monitoring the amount of sanitation material in the sanitation material dispenser; and transmitting an alert from the electronic multifunction device to a remote computer when the sanitation material falls below a predetermined level.

2. The method of claim 1, the transmitting further including transmitting location data in order to identify the location of the sanitation material dispenser.

3. The method of claim 1 further comprising automatically ordering, from the remote computer, additional sanitation material to be delivered to the sanitation material dispenser.

4. The method of claim 1 further comprising:

providing a dryer for dispensing dryer material, the electronic multifunction device further operable to monitor the amount of dryer material remaining in the dryer;

monitoring the amount of dryer material remaining in the dryer; and transmitting an alert from the electronic multifunction device to a remote computer when the dryer material falls below a predetermined level.

5. The method of claim 4 wherein the monitoring of the dryer and the sanitation material dispenser is conducted in real time.

* * * * *